United States Patent [19]

Harrigan

[11] Patent Number: 4,807,937

[45] Date of Patent: Feb. 28, 1989

[54] JUMPSUIT SUPPORT

[76] Inventor: Linda M. Harrigan, 1201 Eric Ct., Rohnert Park, Calif. 94928

[21] Appl. No.: 114,736

[22] Filed: Oct. 29, 1987

[51] Int. Cl.$^4$ ............................................. A47C 31/00
[52] U.S. Cl. .................................... 297/465; 128/874; 297/473
[58] Field of Search ...................... 297/465, 473, 465; 128/134; 24/386, 616, 617, 3 K, 419, 429

[56] References Cited

U.S. PATENT DOCUMENTS

| | | | |
|---|---|---|---|
| 856,480 | 6/1907 | Long | 24/616 |
| 3,641,997 | 2/1972 | Posey | 128/134 |
| 4,170,991 | 10/1979 | Kella | 297/467 X |
| 4,657,005 | 4/1987 | Williamson | 128/134 |
| 4,685,454 | 8/1987 | Posey | 128/134 |

FOREIGN PATENT DOCUMENTS

| | | | |
|---|---|---|---|
| 2227454 | 1/1974 | Fed. Rep. of Germany | 297/465 |
| 2607006 | 9/1976 | Fed. Rep. of Germany | 24/386 |
| 728849 | 4/1955 | United Kingdom | 297/465 |

Primary Examiner—James T. McCall

[57] ABSTRACT

A jumpsuit style support and restraint garment designed to safely and comfortably confine a person to a chair or wheelchair while providing proper body alignment and allowing full range of motion of arms and legs. A human body fitting cloth panel with front and shoulder covering has a rib-knit V-neck in the top. A bottom fold having rib-knit lined leg holes frontwardly horizontally aligned is a seat portion and a continuation of the panel which can be passed under the back rest of a wheelchair. The panel continues as a back member which extends up the outside backrest of the wheelchair and is zipper-fastened to the shoulder covering behind the patient's neck. A special locking ring prevents the patient from easily unzipping the fasteners. Movement of the support materials is restricted by handle apertures which fit the wheelchair handles. Full pants and shorts styles are available in the jumpsuit design.

4 Claims, 2 Drawing Sheets

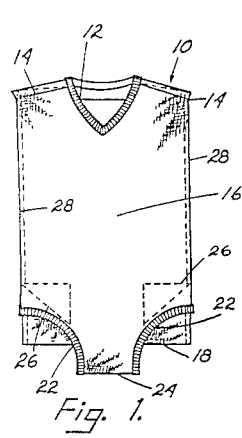
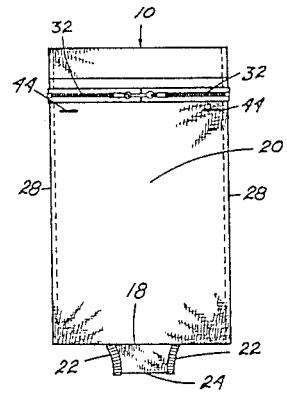
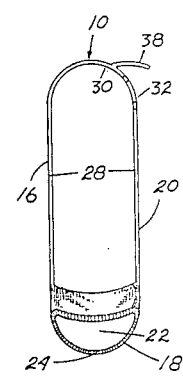
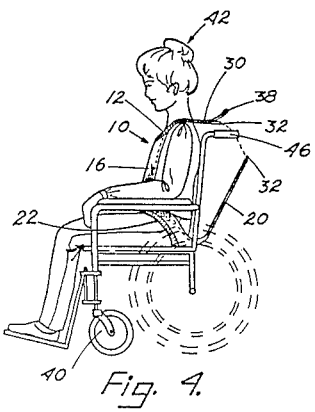
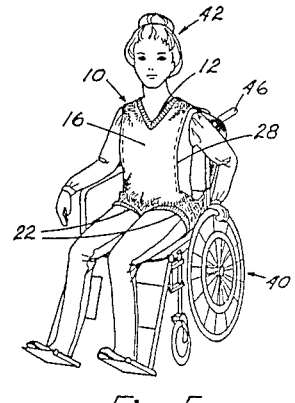
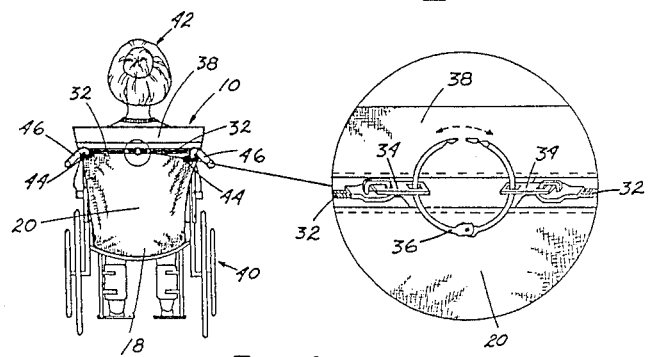

JUMPSUIT SUPPORT

BACKGROUND OF THE INVENTION

1. Field of the Invention

This invention relates to devices which are designed to support a person within a chair or wheelchair in a comfortable yet restrained condition.

2. Description of the Prior Art

Past art patents were examined from a search conducted in the following classes and subclasses:

297/464, 467, 465, 466, and 297/Dig. 4.

The following patents appeared to me to be most pertinent to my invention:

Givens was issued U.S. Pat. No. 2,767,403, dated Oct. 23, 1956, and shows a high chair bib for children.

U.S. Pat. No. 3,099,486, was issued to Scott on July 30, 1963 for a safety car seat.

Pat. No. 3,181,530, dated May 4, 1965, was issued to Storey and illustrates a vest-type support which is designed to restrain or inhibit motion of a person.

On June 29, 1965, Kendell was issued U.S. Pat. No. 3,191,599, for a belt type restraining harness.

Kella was issued U.S. Pat. No. 4,170,991, dated Oct. 16, 1979, on the "seat bib", which is designed to prevent a person from sliding down and out of a chair.

The Flamm patent dated Nov. 18, 1980, U.S. Pat. No. 4,234,228, shows a seating system comprised of three foldable sections of frame with foam pads and an accessory vest plate.

A patent issued to Legan on May 18, 1982, U.S. Pat. No. 4,330,152, illustrates a support and restraint apron.

U.S. Pat. No. 4,509,797, issued to Mullaly on Apr. 9, 1985, discloses a wheelchair restraint which is attached to the persons thighs.

On Feb. 18, 1986, Holder was issued U.S. Pat. No. 4,571,000, and shows a vest type restraining garment.

To may knowledge, the previous patents represent devices most pertinent to my invention. Although many support and restraining devices are currently available, a number a deficiencies arise in their design which include, lack of comfort, lack of safeguards to prevent the person from releasing himself from the device, and lack of design of the garment which helps maintain proper body alignment of the person being confused. My invention not only overcomes the forgoing mentioned deficiencies but allows the person normal range of motion of his arms and legs while in a sitting position and prevents sliding down and out of the chair or wheelchair. My device is manufactured of selected, durable cloth and is easy and quick to apply having only two connecting zippers instead of a maze of belts and buckles. The second embodiment of my invention is designed to be worn in place of trousers and therefore is visually more similar to regular street clothes which, therefore, would be more acceptable to the wearer and their families than a device looking like a restraint jacket. Therefore, there were no devices found in the search which were in close proximity with my device.

SUMMARY OF THE INVENTION

In practicing my invention, I have developed a durable cloth jumpsuit style support and restraint device structured for people to prevent falls and maintain proper body alignment while providing comfort and normal range of motion of the arms and legs with the user in a sitting position.

My invention is designed to be worn like a jumpsuit garment with the person's legs fitting into two flexible openings at the bottom of the device, while the front panel is pulled up and over their head. The back panel extends behind the person and has apertures which fit over the handles of a wheelchair to help secure the upper portion of jumpsuit support in a vertical position. The back panel extends through the rear frame of the wheelchair, which prevents the wearer from sliding forward, and is joined with the front panel near the back shoulders with two zippers. The zippers have an accessory security snap ring designed to prevent the wearer from inadvertently opening the zippers and removing the garment. My jumpsuit support is also provided in models where the leg openings are fitted with slack-type pant leg extensions and in styles similar to shorts.

Therefore, it is a primary object of my invention to provide a jumpsuit style support and restraint device for use in a sitting position as in a wheelchair.

Another object of my invention is to provide a jumpsuit style support and restraint device which maintains proper body alignment.

A further object of my invention is to provide a jumpsuit style support and restraint device with safety features that prevent the wearer from removing the device.

A still further object of my invention is to provide a support and restraint device which is comfortable and avoids constricting any part of the body, therefore preventing tissue damage.

Some of the objects of my invention have been stated and others will prove evident from reading the description of the number parts in the specification and comparing them with similar numbered parts shown in the accompanying drawings.

BRIEF DESCRIPTION OF THE DRAWINGS

FIG. 1 shows a frontal view of the preferred embodiment vertically positioned with the neck opening in the top and the leg openings at the bottom.

FIG. 2 shows a back view of FIG. 1.

FIG. 3 is a side view of the jumpsuit support and restraint showing the wide arm openings in the sides and the leg openings at the bottom.

FIG. 4 shows a side view of the invention in the process of securing a person to a wheelchair.

FIG. 5 shows a perspective view of the device in use securing a person within a wheelchair.

FIG. 6 shows a rear view of the applied device with an enlargement of the safety snap ring in use attached to two zipper sliders.

Figure 7:
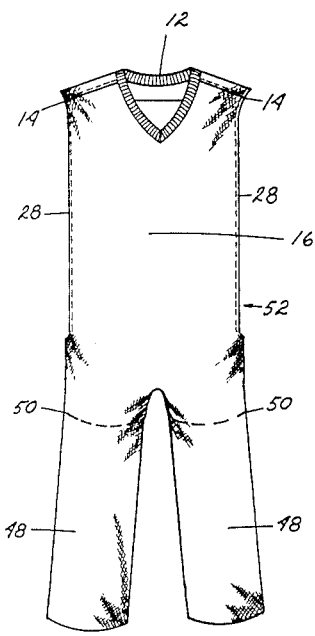
FIG. 7 shows a frontal view of the second embodiment of the invention illustrating slack-type pant legs used and indicating cut-off for short pant leg styling.

DRAWING REFERENCE NUMBERS 10 jumpsuit support and restraint body
12 rib-knit V-neck opening
14 shoulder darts
16 body fitting front
18 bottom folds
20 back
22 rib-knit leg holes
24 crotch strip 26 leg darts
28 trimmed side openings
30 shoulder continuation
32 zippers
34 zipper sliders
36 security snap ring
38 zipper cover flap
40 wheelchair
42 person
44 handle apertures
46 chair handles
48 slack-type pant legs
50 cut-off for short pant leg style
52 coverall support body

DESCRIPTION OF THE PREFERRED EMBODIMENT

Referring now to the drawings at FIG. 1 where the preferred embodiment of the invention is illustrated, showing the durable cloth jumpsuit support and restraint body 10 in a frontal view. Rib-knit V-neck opening 12 is positioned at the top of the garment with shoulder darts 14 extending from the rib-knit V-neck opening 12 downwardly to the trimmed side openings 28, shown in FIG. 3. Torso fitting front 16 extends down to crotch strip 24 and continues on to bottom fold 18 and ends up with back 20, as shown in FIG. 1 and 2. Rib knit leg holes 22 are situated on either side of crotch strip 24 and are located beneath leg darts 26, as seen in FIG. 1. Torso fitting front 16 extends back to shoulder continuation 30, which extends further to zipper cover flap 38, illustrated in FIG. 2. Shoulder continuation 30 is attached to zippers 32 which contain zipper sliders 34, also illustrated in FIG. 2. Zipper sliders 34 are secured in the closed position by security snap ring 36, as seen in FIG. 6. Back 20 has located on its upper edge, two handle apertures 44, seen in FIG. 2, which are designed to fit over chair handles 46 of wheelchair 40, shown in FIG. 6.

Figure 8:
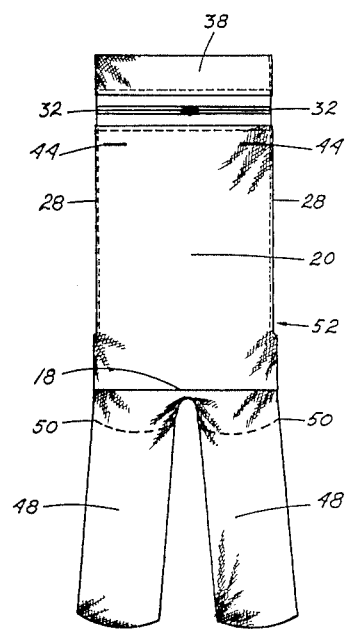
FIG. 8 shows a rear view of the second embodiment.
Figure 9:
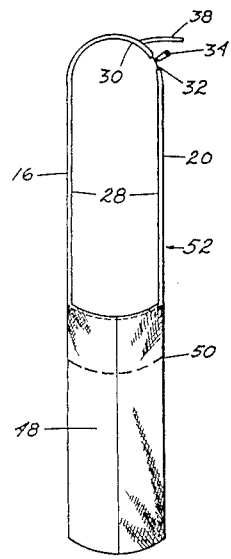
FIG. 9 shows a side view of the second embodiment.
Figure 10:
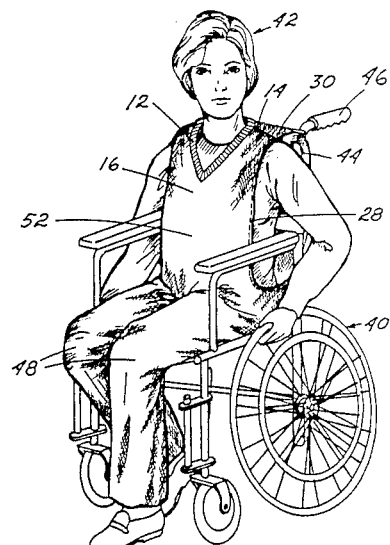
FIG. 10 shows a perspective view of the second embodiment in use securing a person within a wheelchair.

A second embodiment of the invention is shown in FIG. 7, 8, 9, and 10 depicting a downward extension of jumpsuit support and restraint body 10 into slack-type pants legs 48 with a cut-off for shorts 50 indicated constituting the second embodiment designated coverall restraint body 52.

Although there have been preferred embodiment of the invention described in the specifications in precise terms, it is to be understood that references are made in a descriptive sense only and not for the purpose of limiting modifications, as long as such modifications do not exceed the intended scope of the appended claims.

I claim:

1. A support and restraint device for seated human use on chairs and wheelchairs, comprising:

a substantially rectangular durable cloth panel vertically oriented longitudinally and folded twice horizontally forming a single piece front panel, a horizontally split rear panel and upwardly and downwardly looping ends with said horizontally split rear panel removably attached by double zipper and ring locking means adjacently said upwardly looping end;

said upwardly looping end apertured centrally with a V-neck opening having a rib-knit edging therearound;

said downwardly looping end apertured with two rounded rib-knit lined leg holes positioned on either side of a continuing crotch member there being short hip high side panels connecting said front panel to the lower section of said horizontally split rear panel on each side with the remaining openings between said panels providing arm passage for said seated humans;

said horizontally split rear panel having the lower section thereof apertured by two openings in horizontal parallel alignment sized and positioned to fit over and allow passage therethrough of push handles on wheelchairs;

said lower section of said split rear panel arranged to slide through the back opening at the seat of said wheelchair, up the outside of said wheelchair back and attach upwardly to said upper section of said split rear panel removably affixed by said double zipper and ring locking means;

means for protectively covering said double zipper and ring locking means;

said support and restraint device customized to human torso variations and to the needs of individual patients including the addition of short or long pantaloons to said leg holes.

2. The device of claim 1 with said double zipper and ring locking means being two adjacently aligned zipper closures removably attaching said horizontally split sections of said rear panel one to the other with the pull tabs of said zippers attachable outwardly and locking said panels together by inward movement towards each other there being a single snap ring fitting apertures in said pull tabs preventing opening of said zippers without removal of said snap ring.

3. The device of claim 1 wherein said means for protectively covering said double zipper and ring locking means is a horizontally aligned flap having an upwardly edge hingedly sewn transversing said upper section of said horizontally split rear panel immediately above said zipper connection with said flap having a downwardly free edge and being of sufficient width to cover said double zipper and ring locking means.

4. The device of claim 1 with said zipper closures being metal, plastic, and various combinations thereof.

* * * * *